(12) United States Patent
Leeper et al.

(10) Patent No.: US 7,977,305 B2
(45) Date of Patent: *Jul. 12, 2011

(54) JUVENILE HORMONE COMPOSITIONS AND METHODS FOR MAKING SAME

(75) Inventors: Timothy Jon Leeper, Greensboro, NC (US); Joy Michelle Thomas, Graham, NC (US); Amy Marie Nichols, Greensboro, NC (US)

(73) Assignee: ProvisionGard Technology LLC

( * ) Notice: Subject to any disclaimer, the term of this patent is extended or adjusted under 35 U.S.C. 154(b) by 1009 days.

This patent is subject to a terminal disclaimer.

(21) Appl. No.: 11/749,406

(22) Filed: May 16, 2007

(65) Prior Publication Data
US 2007/0212383 A1 Sep. 13, 2007

Related U.S. Application Data

(63) Continuation of application No. 10/658,789, filed on Sep. 10, 2003, now Pat. No. 7,250,396, which is a continuation-in-part of application No. 10/356,731, filed on Feb. 3, 2003, now Pat. No. 7,204,994.

(51) Int. Cl.
*A01P 7/04* (2006.01)
(52) U.S. Cl. ......... 514/2; 424/400; 504/116.1; 514/506; 514/512; 530/399
(58) Field of Classification Search .................. None
See application file for complete search history.

(56) References Cited

U.S. PATENT DOCUMENTS

| | | |
|---|---|---|
| 3,961,051 A | 6/1976 | Emodi |
| 4,303,642 A | 12/1981 | Kangas |
| 4,774,090 A | 9/1988 | Fekete et al. |
| 4,818,536 A | 4/1989 | Meyers et al. |
| 4,948,586 A | 8/1990 | Bohm et al. |
| 5,023,247 A | 6/1991 | Boulanger et al. |
| 5,089,259 A | 2/1992 | Wessling |
| 5,154,749 A | 10/1992 | Dorman et al. |
| 5,188,824 A | 2/1993 | Wessling et al. |
| 5,194,263 A | 3/1993 | Chamberlain et al. |
| 5,225,192 A | 7/1993 | Lovrecich |
| 5,260,259 A | 11/1993 | Dorman et al. |
| 5,460,817 A | 10/1995 | Langley et al. |
| 5,476,652 A * | 12/1995 | Chinuki et al. ............ 424/78.01 |
| 5,560,909 A | 10/1996 | Rheaume et al. |
| 5,567,430 A | 10/1996 | Levy |
| 5,688,509 A | 11/1997 | Radwan et al. |
| 5,690,951 A | 11/1997 | Lew et al. |
| 5,705,175 A | 1/1998 | Johnson |
| 5,707,639 A | 1/1998 | Owaga et al. |
| 5,750,126 A | 5/1998 | Smith et al. |
| 5,787,686 A | 8/1998 | Bott et al. |
| 5,843,215 A | 12/1998 | Whalon et al. |
| 5,849,320 A | 12/1998 | Turnblad et al. |
| 5,869,074 A | 2/1999 | Morrison et al. |
| 5,965,123 A | 10/1999 | Ahmed |
| 6,093,415 A | 7/2000 | Karr et al. |
| 6,123,756 A | 9/2000 | Poppen et al. |
| 6,346,261 B1 | 2/2002 | Sembo |
| 6,365,066 B1 | 4/2002 | Podszun et al. |
| 6,395,776 B1 | 5/2002 | Losel et al. |
| 6,419,943 B1 | 7/2002 | Sakurada et al. |
| 6,436,421 B1 | 8/2002 | Schindler et al. |
| 7,204,994 B2 * | 4/2007 | Leeper et al. ................ 424/400 |
| 7,250,396 B2 * | 7/2007 | Leeper et al. ................ 424/400 |

FOREIGN PATENT DOCUMENTS

| | | |
|---|---|---|
| EP | 0 851 008 A2 | 7/1998 |
| WO | 97/29638 A | 8/1997 |
| WO | 98/33821 A1 | 8/1998 |
| WO | 99/18134 A1 | 4/1999 |
| WO | 99/32088 A1 | 7/1999 |
| WO | 01/10212 A | 2/2001 |

OTHER PUBLICATIONS

Shanjahan et al. Effect of Methoprene Coated Papers as an Insect Resistant Packaging Material on Three Stored Product Pest. Nuclear Science and Applications. Jan. 1991, vol. 3, No. 1, pp. 23-26.
International Search Report in Appl. No. PCT/US04/03077.
Written Opinion of the ISA for International Appl. No. PCT/US04/03077.
Printing Industry , "Gravure" http://www.wmrc.uiuc.edu/manuals/printing/gravure.htm (Aug. 2002).
http://www.wmrc.uiuc.edu/manuals/printing/images/ch8fig10.jpg (gravure figure) (Aug. 2002).
Printing Industry, "Flexography", http://www.wmrc.uiuc.edu/manuals/printing/flexography.htm (Aug. 2002).
http://www.wmrc.uiuc.edu/manuals/printing/images/ch7fig9.jpg (figure) (Aug. 2002).
Shore, Marvin, "Toll Manufacturing Beneficial for Pesticidal Coatings" Paint & Coatings Industry (Jul. 2002).
Henrick, C.A., et al. "Values on Sensitive Synchronized Instars" pp. 56-58.
Pesticide Action Network Pesticide Database http://www.pesticideinfo.org./PCW/Detail.sub.--Product.Jsp?REG.sub.--0027-2400467&DIST.sub.--NR (Aug. 2002).
Office of Pesticide Programs "Larvicides for Mosquito Control" http://www.epa.gov/pesticides/citizens/larvicides4mosquitos.htm (Aug. 2002).
Pesticide Action Network "Pesticide Product Search" http://www.pesticideinfo.org./PCW/List.sub.--Products.sub.--Adv.jsp (Aug. 2002).
Pesticide Action Network "Chemical Information about Buprofezin" http://www.pesticideinfo.org/PCW/Detail.sub.--Chemical.JSP?Reg.sub.--Id=P- C35811 (Aug. 2002).

(Continued)

Primary Examiner — Anish Gupta (57) ABSTRACT

The present invention relates to hormone coating layers having desirable hormone delivery characteristics and product lifetime. In one embodiment, the invention is a hormone composition including a substrate having an external surface, and a coating layer disposed on the external surface. The coating layer preferably includes a polymer web, and from about 1 wppm to about 100,000 wppm of a hormone comprising a terpene dispersed throughout the polymer web. The invention also relates to methods for making hormone coating materials of the present invention. The coating compositions of the present invention preferably are implemented in human and animal food packaging materials in order to safely and efficiently protect the foodstuffs contained therein from insect infestation.

37 Claims, 4 Drawing Sheets

OTHER PUBLICATIONS

Pesticide Action Network "Actinic, Inc.—Dimilin-2f" http://www.pesticideinfo.org/PCW/Product.sub.--jsp?Reg.sub.--NR=000400004- 73&DIST.sub.--NR (Aug. 2002).

Pesticide Action Network "Actinic, Inc.—Dimilin 25w for cotton/soybean" http://www.pesticideinfo.org/PCW/ProductsJSP?Reg.sub.--NR00040000465&DIST- .sub.--NR (Aug. 2002).

Pesticide Action Network Actinic, Inc.-"Pesticide Product Search" (Prods. containing Dimilin). http://www.pesticideinfo.org./PCW/List.sub.--Products.sub.--Adv.jsp? (Aug. 2002).

Pesticide Action Network "Dimilin w-25 for pasture grass mosquitoes" http://www.pesticideinfo.org/PCW/Detail.sub.--Product.jsp?REG.sub.--NR=00- 040000470&DIST.sub.--NR (Aug. 2002).

Pesticide Action Network "Chemical Information about Fenoxycarb" http://www.pesticideinfo.org/PCW/Detail.sub.--Chemical.jsp?Rec.sub.--Id=P- C33190 (Aug. 2002).

Pesticide Action Network "Pesticide Product Search" (U.S. Registered Prods. containing Fenoxycarb). http://www.pesticideinfo.org/PCW/List.sub.--Products.sub.---Adv.jsp? (Aug. 2002).

Pesticide Action Network "Chemical Information about Hexaflumuron" http://www.pesticideinfo.org./PCW/Detail.sub.--Chemical.jsp?Rec.sub.--Id+- PC35740 (Aug. 2002).

Pesticide Action Network "Pesticide Product Search" (U.S. Registered Prods. containing (7S)-Hydroprene). http://www.pesticideinfo.org./PCW/List.sub.--Products.sub.--Adv.jsp? (Aug. 2002).

Pesticide Action Network "Pesticide Product Search" (U.S. Registered Prods. containing Hydroprene). http://www.pesticideinfo.org./PCW/List.sub.--Products.sub.--Adv.jsp? (Aug. 2002).

Pesticide Action Network "Chemical Information about Kinoprene" http://www.pesticideinfo.org./PCW/Detail.sub.--Chemical.jsp?Rec.sub.--Id=- PC32982 (Aug. 2002).

Pesticide Action Network "Pesticide Product Search" (U.S. Registered Prods. containing Methoprene). http://www.pesticideinfo.org./PCW/List.sub.--Products.sub.--Adv.jsp? (Aug. 2002).

Pesticide Action Network "Chemical Information about Methoprene" http://www.pesticideinfo.org./PCW/Detail.sub.--Chemical.jsp?Rec.sub.--Id=- PC32837 (Aug. 2002).

Environmental Protection Agency "Pesticide Fact Sheet" Jun. 2001 Update of the Mar. 1991 Methoprene R.E.D. Fact Sheet pp. 1-9.

Office of Pesticide Programs Biopesticide Fact Sheet, Insect Growth Regulators, S-Hydroprene, S-Kinoprene, Methoprene, S-Methoprene http://www.epa.gov/pesticides/biopesticides/factsheets/fs-insect-grow-reg- .htm.htm (Aug. 2002).

Pesticide Action Network "Pesticide Product Search" (U.S. Registered Prods. containing Tebufenozide). http://www.pesticideinfo.org./PCW/List.sub.--Products.sub.--Adv.jsp? (Aug. 2002).

Pesticide Action Network "Chemical Information about Tebufenozide" http://www.pesticideinfo.org./PCW/Detail.sub.--Chemical.jsp?Rec.sub.-Id=- PC36018 (Aug. 2002).

Pesticide Action Network "Confirm 2f agricultural insecticide" http://www.pesticideinfo.org./PCW/Detail.sub.--Chemical.jsp?Reg.sub.--NR=- 06271900420&DIST.sub.--NR (Aug. 2002).

Pesticide Action Network "Rh-5992 technical insecticide" http://www.pesticideinfo.org./PCW/Detail.sub.--Product.jsp? Reg.sub.--NR=0- 6271900419&DIST.sub.--NR (Aug. 2002).

Los Angles County-Department of Health Services "Controlling Stored Product Pests" pp. 1-3.

Index for the Interpretive Line Slides for Insects, Chapter 13 "Indianmeal Moth", http://ww.okstate.edu/OSU.sub.--Ag/agedcm4h/pearl/e912/ch13/ch13/c- h13f8.htm (Mar. 2000).

Insect Growth Regulators and Insect Development "Chemical Structure and Function" http://www.zoo.utoronto.ca/zoo344s/group2/chemical.htm (Aug. 2002).

The Insect Life Cycle Chapter 4, 156-158 (Metamorphosis).

Today's Breeder Magazine, Issue 23 "Today's Breeder Wants to Know" http://www.purina.com/breeders/magazine.asp?article=278 (Aug. 2002).

ARS News & Information "Protecting Perishables from Package Pests" http://www.ars.usda.gov/is/pr/2002/020111.2htm (Aug. 2002).

Arthur, Franklin, et al "Insect Pest Management in Stored Bulk Grains and Seeds: Reduced Risk-Insecticides and Non-Chemical Controls" pp. 1-2.

Arthur, Frank, et al Science Direct Impact of high temperature on efficacy of cyfluthrin and hydroprene applied to concrete to control Tribolium castaneum (Herbst)*1 http://www.sciencedirect.com/science?.sub.--ob=ArticleURL&.sub.--udi=B6T8- Y-44VWXFD-1&.sub.--user (Aug. 2002).

Kramer, Bettina, et al., Science Direct "Differentially expressed genes in metamorphosis and after juvenile hormone application in the pupa of Galleria" http://www.sciencedirect.com/science?.sub.--ob=ArticleURL&udiB6-t79-446NC5-4&sub.--user=1 (Aug. 2002).

Silhacek, D., et al., Science Direct "Behavior and movements of Indian meal moths (Plodia interpunctella Hubner) during commodity infestation" http://www.sciencedirect.com/science?.sub.--ob=ArticleURL&sub.--reqID=75- 48602.sub.--acct=C0000502 (Aug. 2002).

Office of Pesticide Programs "Biopesticide Fact Sheet, Plant Oils" http://www.epa.gov/pesticides/biopesticides/factsheets/fs.sub.--plaint.su- b.--oils.htm (Aug. 2002).

Environmental Protection Agency "Registration Eligibility Document, Isopropyl (2E, 4E)-11-Methoxy-3,7, 11-Trimethy1-2,4, Dodecadienoate (Referred to as Methoprene)" (Mar. 1991).

Ahmad et al., "Effect of Tyroxine and Juvenile Hormone Analog on Haemolymph Ecdysteroid Titer Pattern During Fifth Instar of Bombyx mori (Lepidopter: Bombycidae)", http://esa.confex.com/esa/2001/techprogram/paper.sub.--1079.htm (Dec. 2001).

Bloomquist, Jeffrey R., "Insecticides: Chemistries and Characteristics", http://ipmworld.umn.edu/chapters/bloomq.htm (Aug. 2002).

Chidambar, S., "Flexography Versus Rotogravure", http://www.indianprinterpublisher.com/aug/archive-ipp/archive2001/packagi- ng2001/flexograpl (Feb. 2003).

Henrick et al., "Structure Activity Relationships in Some Juvenile Hormone Analogs", Zoecon Research Laboratories, Palo Alto, California.

Williams, C.M. "Juvenile Hormone . . . In Retrospect and in Prospect", The Juvenile Hormones, ed. L. I. Gilbert, pp. 1-12. New York: Plenum Press (1976).

Hydroprene General Fact Sheet, National Pesticide Information Center, Oregon State University, Corvallis, Oregon (Apr. 2002).

Si-Cal's Guide to Flexographic and Graavure Printing, http://www.si-cal.com/gravure.html (Feb. 2003).

Pesticide Action Network Pesticide Database, http://www.pesticideinfo.org/List.sub.--Chemicals.jsp? (Jan. 2003).

Extoxnet Extension Toxicology Network, http://pmep.cce.cornell.edu/profiles/extoxnet/haloxyfop-methylparathion/m-ethoprene-ext.html (Aug. 2002).

Wicks, Zeno W., "What Are Coatings? Compositions of Coatings", Organic Coatings: Science and Technology, p. 4 (1999).

Supplementary European Search Report for European Patent Application EP 04 70 7761.

* cited by examiner

Example 3
Exposure of 16 Day Indian Meal Moth Larvae to Methoprene

Fig. 3

JUVENILE HORMONE COMPOSITIONS AND METHODS FOR MAKING SAME

CROSS-REFERENCE TO RELATED APPLICATION

This application is a continuation of U.S. patent application Ser. No. 10/658,789, filed Sep. 10, 2003, which is a continuation-in-part of U.S. patent application Ser. No. 10/356,731, filed Feb. 3, 2003, now U.S. Pat. No. 7,204,994, the entireties of which are incorporated herein by reference.

FIELD OF THE INVENTION

This invention relates to an approach for preventing pest infestation, and more particularly, to hormone compositions and specifically to hormone coating layers for use with food packaging substrate materials.

BACKGROUND OF THE INVENTION

The infestation of food products by insects and insect larvae is well-documented. One particularly destructive pest is the Indian Meal Moth, *Plodia Interpunctella*, which is known to infest stored commodities, processed foods packaged for human consumption, and products produced for the pet food and birdseed markets. Infestations often remain hidden until the final larval stage, called the wandering phase, begins in which the larvae begin to search for a pupation site. Most Lepidopteran larvae become more tolerant of insecticides as they age. As a result, wandering-phase Indian Meal Moth larvae can be difficult to control.

Conventionally, coatings which repel insects, discourage feedance and deter oviposition have been implemented on food product packaging materials. For example, U.S. Pat. No. 5,843,215 to Whalon et al. is directed to coatings which comprise a water-based or water soluble resin and plant secondary compounds. The plant secondary compounds consist of those compounds which have insecticidal characteristics, such as insect repellence, antifeedance and oviposition deterrence.

U.S. Pat. No. 5,688,509 to Radwan et al. is directed to a controlled-release insect repellant device and a method for repelling insects from food, tobacco, or other consumable items. The device comprises an insect repellent composition contacting a substrate. The device is prepared by a method comprising applying the insect repellent composition to the substrate wherein the repellent compound used is present in the controlled-release insect repellent device in an amount such that when it is released it is non-toxic to humans and animals. The method for repelling insects comprises placing the controlled-release insect repellent device in an area where insects may be present. The insect repellent composition comprises a repellent compound and a controlled-release agent which comprises a compound which may be synthetic and/or natural, and, optionally, a solvent. The repellent compound may be chosen from the group consisting of essential oils and active ingredients of essential oils.

Although pesticidal compounds have been used with some success on food packaging materials, the toxicity of these compounds often renders them unsuitable for use on food packaging materials. Some insect juvenile hormones, their analogues and their derivative compounds, present less toxicity than conventional pesticidal compounds. Juvenile hormones are insect growth regulators, which interfere with the developmental process of immature insects, but do not necessarily kill adult insects. In February 2002, the insect growth regulator methoprene was relabeled for stored commodities at application rates of 1, 2.5 and 5.0 ppm.

Methoprene and many other hormones are relatively volatile. As a result, conventional means for delivering a pesticidal compound may be undesirable for delivering a hormone because the hormone may volatize at an undesirably fast rate thereby providing an unsatisfactory product lifetime. Accordingly, a need exists for new hormone coating formulations and methods for making same, which provide coating layers having desirable hormone delivery characteristics and product lifetime.

SUMMARY OF THE INVENTION

The present invention provides hormone coating layer compositions having desirable hormone delivery characteristics and product lifetime. The coating compositions of the present invention preferably are implemented in human and animal food packaging materials in order to safely and efficiently protect the foodstuffs contained therein from insect infestation. In one embodiment, the invention is to a method for forming a hormone coating composition, the method comprising the steps of: providing a substrate having an external surface; providing a liquid coating material comprising a polymer, a polymer carrier, and from about 1 wppm to about 100,000 wppm of a hormone, wherein the hormone comprises a terpene; applying the liquid coating material to the external surface of the substrate to form a liquid coated substrate; and removing the polymer carrier from the liquid coated substrate under conditions effective to form a solid coated substrate.

In another embodiment, the invention is to a hormone composition, comprising: a substrate having an external surface; and a coating layer disposed on the external surface, wherein the coating layer includes a polymer web, and from about 1 wppm to about 100,000 wppm of a hormone comprising a terpene dispersed throughout the polymer web. Optionally, the hormone composition further comprises a glue material. In one aspect, the coating layer optionally forms a package seal.

Optionally, the hormone is a juvenile hormone, which may comprise, for example, hydroprene, methoprene, kinoprene or triprene. In one aspect, the liquid coating material further comprises from about 0.01 weight percent to about 20 weight percent diatomaceous earth. In this aspect, the process optionally further comprises agitating the liquid coating material under conditions effective to distribute the diatomaceous earth throughout the liquid coating material.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

The present invention relates to hormone coating compositions, each of which provides a coating layer having desirable hormone delivery characteristics and product lifetime. The invention also relates to methods for making hormone coating materials of the present invention. The coating compositions of the present invention preferably are implemented in human and animal food packaging materials in order to safely and efficiently protect the foodstuffs contained therein from insect infestation.

In one embodiment, the present invention is directed to a hormone composition that includes a substrate having an external surface, and a coating layer disposed on or adhered to the external surface. The coating layer comprises a polymer web, a UV protectant material, and from about 0.01 wppm to about 10 weight percent of a hormone dispersed throughout the polymer web. More specifically, in terms of lower range limits, the coating layer comprises at least about 0.01 wppm, more preferably at least about 0.1 wppm, more preferably at least about 1 wppm, more preferably at least about 10 wppm, and most preferably at least about 100 wppm of the hormone. In terms of upper range limits, the coating layer comprises about 10 weight percent or less, more preferably about 5 weight percent or less, more preferably about 1 weight percent or less, more preferably about 100,000 wppm or less, and most preferably about 10,000 wppm or less of the hormone. Thus, a coating layer according to the present invention may include from about 0.01 wppm to about 5 weight percent, from about 0.01 wppm to about 1 weight percent, from about 1 wppm to about 100,000 wppm, from about 1 wppm to about 10,000 wppm, or from about 10 wppm to about 10,000 wppm of a hormone, or any other combination of the above-provided hormone range limitations. Ideally, the coating layer comprises from about 100 wppm to about 10,000 wppm of a hormone.

As used herein, the term "weight percent" means percent, by weight, of a specified composition based on the total weight of a coating layer in accordance with the present invention. Similarly, the term "wppm" means parts per million, by weight, of a specified composition based on the total weight of a coating layer according to the present invention. Unless otherwise indicated, the terms "weight percent" and "wppm" of a specified composition are based on the total weight of the dry (in the solvent based coating) or cured (in the UV based coating) form of the coating layer rather than the total weight of a pre-application coating formulation. Also, the term "coating layer" means a substantially solid coating disposed on a substrate, and the term "coating formulation" means a composition suitable for application onto a substrate and being capable of forming a coating layer.

A variety of hormones may be implemented in the coating layers of the present invention. As used herein, the term "hormone" includes naturally or non-naturally occurring hormones, analogues and mimics thereof. A non-limiting list of types of hormones includes insect growth regulators, juvenile hormones, chitin synthesis inhibitors, ecdysteroids and ecdysone agonists. An exemplary non-limiting list of insect growth regulators includes: buprofezin, cyclopentadecatriene, cydia pmonella granulosis virus, dicyclanil, hexahexyl distannoxane, hexythiazox, Ovex, and poly-i-para-menthene. Particularly preferred hormones suitable for use in the present invention include hydroprene, methoprene, dimilin and fenoxycarb.

Preferably, the hormone comprises a juvenile hormone. As used herein, the term "juvenile hormone" includes naturally and non-naturally occurring juvenile hormones as well as analogues and mimics thereof Naturally occurring juvenile hormones are lipophilic sesquiterpenoids containing an epoxide and methyl ester groups. Juvenile hormone analogues are compounds bearing a structural resemblance to the juvenile hormones of insects. A non-limiting list of juvenile hormone analogues suitable for use in the present invention includes: pyriproxyphene: 4-phenoxyphenyl-(RS)-2-2(2-pyridyloxy)propyl ether; fenoxycarb: ethyl {2-(4-fenoxy-fenoxy)ethyl}carbamate; kinoprene: 2-propynyl-(E)-3,7,11-trimethyl-2,4-dodecadienoate; methoprene: isopropyl-(2E,4E)-11-methoxy-3,7,11-trimethyl-2,4-dodecadienoate; and hydroprene: ethyl-(E,E)-(R,S)-3,7,11-trimethyldodeca-2,4-dienoate. Thus, the hormone contained in the coating of the present invention may include naturally or non-naturally occurring juvenile hormones such as methoprene, hydroprene, triprene, furnesinic acid ethyl and alkoxy derivatives, pyriproxyfen (Nylar), and fenoxycarb. Particularly preferred juvenile hormones suitable for use in the present invention include hydroprene, methoprene, and fenoxycarb. As methoprene bears a close structural resemblance to naturally occurring juvenile hormones, it is the most preferred juvenile hormone of the present invention.

In another embodiment of the present invention, the hormone comprises a chitin synthesis inhibitor. As used herein, the term "chitin synthesis inhibitor" includes naturally and non-naturally occurring chitin synthesis inhibitors as well as analogues and mimics thereof. Chitin synthesis inhibitors are classified as benzoylphenylureas and possess a number of halogen substituents. The exoskeleton (cuticle) of insects is formed mostly of protein and chitin. Chitin is a polysaccharide of N-acetylglucosamine. During the process of ecdysis, the old cuticle of an insect is shed and a new one is grown. The production of this compound through a polymerization reaction is halted by inhibitor drugs. Without limiting the scope of the present invention to a particular mechanism, the mode of action of these inhibitors is believed to include the blocking of UDP-N-acetylglucosamine transport through the membrane. Without the ability to produce chitin, an insect is unable to hatch or fails to develop due to its malformed cuticle. By retarding the process of chitin growth it is possible to render invertebrates non-viable as reproductive or adult organisms. Chitin synthesis inhibitors may be transferred to insect eggs before deposition from parental blood if the parent insect has ingested the inhibitor or after deposition through contact with a host. Exposed eggs fail to hatch or produce non-viable larvae. A non-limiting list of exemplary chitin synthesis inhibitors includes: triflumeron, chlorfluazuron, lufenuron, teflubenzuron, flufenoxuron, N-2,6-difluorobenzoyl-N'-[2-fluoro-4-(1,1,2,3,3,3-hexafluoropropoxy)phenyl]urea and N-2,6-difluorobenzoyl-N'-[2-fluoro-4-(1,1,2,2-tetrafluoroethoxy)phenyl]urea, hexaflumuron and other acyl ureas, diflubenzuron (dimilin), and azadirachtin.

Additionally or alternatively, the hormone comprises an ecdysone agonist. As used herein, the term "ecdysone agonist" includes naturally and non-naturally occurring ecdysone agonists as well as analogues and mimics thereof Ecdysone agonists are compounds bearing a close resemblance in action to the invertebrate molting hormone ecdysone. The structures of agonists such as RH-2485 (methoxyfenozide), RH-5849 (dibenzoyl hydrazine) and RH-5992 (Tebufenozide), though different from ecdysone, act through the ecdysone receptor at a molecular level and initiate the molting process through gene regulation. Methoxyfenozide, dibenzoyl hydrazine, and Tebufenozide are considered non-steroidal ecdysone agonists because of their structural variance from ecdysone. However, the hormone implemented in the coating of the present invention may be an ecdysteroid, which causes either molting or metamorphosis depending on the stage of the insect, such as ecdysone, 3-dehydroecdysone, Makisterone A, and 20-hydroxyecdysone. Exposure to ecdysone agonists in larvae, prior to their natural ecdysone peak, results in incomplete molting. After ingestion of the compound, the larva begins to develop a new cuticle. However, the new cuticle lacks tanning and the old cuticle fails to be ecdysed/absorbed. Bursicon is the hormone responsible for the tanning and hardening of the cuticle, but to act, it requires the absence of 20-hydroecdysone. Without limiting the scope of the present invention to any particular mechanism, it is believed that the presence of an edysone agonist inhibits bursicon release. As a result, exposed larvae remain in a state of partial molt until death, and are consequently unable to reproduce.

Optionally, the coatings of the present invention include one or more chemical insecticides or microbial pathogens or toxicants. Examples of toxicants include, but are not limited to, borates (boric acid, disodium octaborate tetrahydrate), mirex, sulfuramid and related fluoroalkyl sulfonamides, hydramethylnon, avermectin, A-9248 (diiodomethyl para-tolyl sulfone), fluorosulfonates, imidacloprid, azadirachtin, and cyromazine.

Many of the above-described hormones, e.g., methoprene, break down when exposed to UV radiation. As a result, the coating layers of the present invention preferably include one or more UV protectant materials, which ideally are non-polymer compositions that absorb UV radiation. Preferably, the coating layer comprises from about 0.01 weight percent to about 20 weight percent, more preferably from about 0.1 weight percent to about 15 weight percent, and most preferably from about 1 to about 10 weight percent of a UV protectant material. Ideally, the UV protectant material is dispersed throughout the polymer web. However, in an alternative embodiment, the UV protectant material is contained in a second coating layer adjacent to the coating layer that contains the hormone composition. Preferably, the second coating layer includes one or more polymers, described herein, which act to support the UV protectant material. In this latter embodiment, the secondary coating layer containing the UV protectant material preferably is oriented externally to the hormone composition coating layer in order to reduce exposure of the hormone coating layer to UV radiation. A non-limiting list of exemplary UV protectant materials that may be included in the coating layers of the present invention includes: benzophenone; hydroxy substituted benzophenones such as 2-hydroxy-4-methoxybenzophenone, 2,2'-dihydroxy-4-methoxybenzophenone, 2-hydroxy-4-acryloyloxyethaxybenzophenone, 2-hydroxy-4-n-octoxybenzophenone and the like; hydroxy phenyl benzopriazdes; substituted acrylonitriles; and selective absorption pigments. A non-limiting list of exemplary selective absorption pigments includes zinc oxide, zinc sulfide, red iron oxide, carbon black, and rutile titanium dioxide. The UV protectant material may also include reflective pigments. Additional UV protectant materials are listed in U.S. Pat. No. 5,965,123, the entirety of which is incorporated herein by reference. Optionally, the coating formulation also includes one or more pigments so that the coating layers may serve as inks in printing processes.

As indicated above, the coating layers of the present invention include a polymer matrix or web. The spaces or cavities within the polymer web or matrix preferably house the hormone in the coating layer, thereby providing desirable controlled release properties of the hormone active ingredient. In one embodiment, the polymers are prepared and incorporated into the coating material before application of the coating material onto the substrate. Alternatively, final polymerization takes place after the coating material has been applied to the substrate.

In one embodiment, the coating formulation of the present invention comprises 90 weight percent or less, more preferably from about 10 weight percent to about 80 weight percent, and most preferably from about 20 weight percent to about 80 weight percent of a monomer or of a monomer emulsion. Preferably, the polymer is formed from one or more acrylated monomers and/or oligomers. A non-limiting list of suitable monomers includes trimethylolpropane triacrylate, methyl acrylate, methyl methacrylate, styrene, acrylonitrile, vinyl acetate, maleic anhydride, vinyl chloride, 1,3-butadiene, isoprene, tetrafluoroethylene, 2(2-ethoxyethoxy)ethyl acrylate, lauryl methacrylate, 2-phenoxyethyl acrylate, isobornyl acrylate, 1,6-hexanediol diacrylate, tripropylene glycol diacrylate, ethoxylated bisphenol A diacrylates, alkoxylated hexanediol diacrylates, trimethylolpropane trimethacrylate, trimethylolpropane triacrylate, tris(2-hydroxy ethyl) isocyanurate triacrylate, ethoxylated trimethylolpropane triacrylates, propoxylated trimethylolpropane triacrylates, propoxylated glyceryl triacrylates, pentaerythritol tetraacrylate, dipentaerythritol pentaacrylate, ethoxylated pentaerythritol tetraacrylates, acrylic acid, methacrylic acid, and their salts, amides, and esters. Thus, the polymer in the coating layer may include one or more of the following polymers: polytrimethylolpropane triacrylate, polymethacrylate, polymethyl methacrylate, polystyrene, polyacrylonitrile, polyvinyl acetate, polymaleic anhydride, polyvinyl chloride, polybutadiene, polyisoprene, polytetrafluoroethylene, poly-2(2-ethoxyethoxy)ethyl acrylate, polylauryl methacrylate, poly-2-phenoxyethyl acrylate, polyisobornyl acrylate, poly-1,6-hexanediol diacrylate, polytripropylene glycol diacrylate, polyethoxylated bisphenol A diacrylates, polyalkoxylated hexanediol diacrylates, polytrimethylolpropane trimethacrylate, polytrimethylolpropane triacrylate, polytris(2-hydroxy ethyl) isocyanurate triacrylate, polyethoxylated trimethylolpropane triacrylates, polypropoxylated trimethylolpropane triacrylates, polypropoxylated glyceryl triacrylates, polypropoxylated glyceryl triacrylates, polypentaerythritol tetraacrylate, polydipentaerythritol pentaacrylate, polyethoxylated pentaerythritol tetraacrylates, polyacrylic acid, and polymethacrylic acid. In one embodiment, the polymer is a copolymer formed from two or more of the above listed monomers.

The polymers in the coating layer are additionally or alternatively formed from one or more oligomers, preferably acrylated oligomers. Bis-phenyl epoxy acrylated oligomers are particularly preferred. Ideally, the oligomers have a molecular weight of from about 50 to about 100,000, more preferably from about 100 to about 20,000. Exemplary oligomers include epoxy acrylates, acrylated urethanes, acrylated polyesters, esterified polyol acrylics, and acrylated oils. If oligomers are included in the coating formulation of the present invention, the coating formulation preferably includes less than about 60 weight percent oligomers, more preferably from about 10 weight percent to about 50 weight percent, and most preferably from about 20 weight percent to about 40 weight percent oligomers.

Preferably, polymerization of the monomers and/or oligomers in the coating formulation is facilitated by a co-initiator. The co-initiator optionally degrades under a Norrish type I or a Norrish type II process. In a preferred initiation mechanism, UV radiation causes electrons in a photoinitiator to enter an excited state. The co-initiator abstracts a hydrogen from the excited photoinitiator thereby forming free radical sites on the photoinitiator and on the co-initiator, which then initiate polymerization of the monomers and/or oligomers in the coating formulation.

In one embodiment, the co-initiator is a tertiary amine. In forming the UV cured embodiment of the present invention, it is believed that oxygen slows the rate of polymerization by forming relatively stable peroxides. Providing tertiary amines in the coating formulation speeds the rate of polymerization thereby minimizing the formation of peroxides. Additionally, the tertiary amine can facilitate chain transfer mechanisms. For example, a hydrogen-abstracted tertiary amine can transfer a radical to another monomer in the coating formulation and initiate the synthesis of another polymer chain. Thus, the presence of a co-initiator reduces oxygen sensitivity and increases the polymerization rate when present in the coating formulation of the present invention. A non-limiting list of exemplary tertiary amine co-initiators includes alkanolamines such as methyl diethanolamine (MDEA), trialkyl amines such as triethylamine (TEA), acrylated tertiary amines, aminoacrylates such as 2-(dimethylamino) ethyl acrylate, and aromatic amines such as esters of 4-dimethyl aminobenzoic acid. Preferably, the coating layer comprises from about 0.1 weight percent to about 15 weight percent, more preferably from about 0.5 weight percent to about 10 weight percent, and most preferably from about 4 weight percent to about 8 weight percent of a co-initiator, which will form polymer chain ends in the cured coating composition.

In one embodiment, the polymers are formed from free radical initiators. The free radical initiators may be selected from one or more of the following groups: peroxides, hydroperoxides, azo compounds, redox initiators, and photoinitiators, which may form free radicals when exposed to visible light or UV radiation. Exemplary peroxide and hydroperoxide initiators include benzoyl peroxide, diacetyl peroxide, di-t-butyl peroxide, and hydroperoxides such as cumyl hydroperoxide. The initiators may also begin polymerization upon exposure to high energy radiation such as $\alpha$- and $\beta$-particles, $\gamma$- and x-rays. The polymers may also be formed by plasma polymerization, wherein polymerization is initiated by a partially ionized gas generated by a radio frequency glow discharge. The polymer also may be formed without an initiator if the monomer itself is sufficiently reactive. For example, styrene, halogenated materials such as chlorinated monomers and polymers (e.g., chlorinated polyesters), methoxy acrylates, methyl methacrylate and some strained-ring cycloalkenes undergo polymerization on heating in the absence of any added free radical initiators.

In one particularly preferred embodiment, a photoinitiator is included in the coating material to initiate polymerization of the monomers and/or oligomers upon exposure to UV radiation. As indicated above, the photoinitiator preferably interacts with a co-initiator, e.g., through hydrogen abstraction, under conditions effective to initiate polymerization. Preferably, the coating layer comprises from about 0.1 weight percent to about 20 weight percent, more preferably from about 0.1 weight percent to about 15 weight percent, and most preferably from about 0.2 weight percent to about 10 weight percent of a photoinitiator. Peroxides and azo compounds dissociate photolytically (as well as thermally).

An advantage of photoinitiation is that the reaction can occur essentially independent of temperature. Moreover, better control of polymerization is realizable because narrow wavelength bands may be used to initiate decomposition of the photoinitiator and begin polymerization. Additionally, the reaction can be stopped simply by removing the UV radiation source. A wide variety of photolabile compounds are available, including, but not limited to, disulfides, benzoin and benzil. A non-limiting list of exemplary photoinitiators includes benzophenone, trimethylbenzophenone, thioxanthone, 2-chlorothioxanthone, 9,10-anthraquinone, and bis-4, 4-dimethylaminobenzophenone (Michler's Ketone). In one embodiment, the photoinitiator is a Type I or Type II photoinitiator. A non-limiting list of Type I photoinitiators includes Benzoin ethers, Benzilketals, .α-Dialkoxyacetophenones, α-Hydroxyalkylphenones (e.g., in combination with benzophenone), .α-Amino alkylphenones (e.g., in combination with thioxanthones), and Acylphosphine oxides. A non-limiting list of Type II photoinitiators includes Benzophenones/amines and Thioxanthones/amines. Benzophenone is a particularly desirable photoinitiator as it also acts as a UV absorber in the final coating layer. In another embodiment, the photoinitiator is a visible photoinitiator, e.g., Titanocenes.

The coating material of the present invention also preferably includes a defoamer or defoaming agent to limit bubble formation in the coating material formulation. Bubble formation in the coating formulation is undesirable because the application of a formulation having bubbles to a substrate results in an uneven formulation profile over the substrate surface. Defoamers reduce the surface tension of the coating formulation so that bubble structures collapse thereby providing desirable processability or manufacturing characteristics. A non-limiting list of exemplary defoamers includes: silicone oils, waxes, fatty acids, solid carriers (e.g., silicates) and fluorinated compounds. If a defoamer is included in the coating material, the coating material preferably comprises from about 0.001 weight percent to about 10 weight percent, more preferably from about 0.01 to about 5.0 weight percent, and most preferably from about 0.1 weight percent to about 1.0 weight percent of a defoamer. In one embodiment, the defoamer comprises.

Additionally, the coating material optionally includes a rheology additive. Rheology additives increase grease resistance and provide desirable controlled release properties for the hormone that is dispersed throughout the polymer web. Without limiting the present invention to a particular mechanism, the rheology agent is believed to facilitate retention of the active ingredient in the coating layer, e.g., the hormone, by slowly releasing the hormone to the environment over the product lifetime. That is, the rheology additive facilitates hormone migration from within the polymer web of the coating layer to the external surface thereof. If a rheology additive is included in the coating material, the coating material preferably comprises from about 0.1 weight percent to about 20 weight percent, more preferably from about 0.1 weight percent to about 10 weight percent, and most preferably from about 0.5 weight percent to about 5 weight percent of a rheology additive. Preferably, the rheology additive is a substituted cellulose acetate composition. A non-limiting list of exemplary rheology additives includes cellulose acetate butyrate (CAB) and cellulose acetate proprionate (CAP).

In one particularly desirable embodiment, the coating layer of the present invention includes inert dusts such as silica dusts, e.g., diatomaceous earth, and zeolitic compositions (alkali metal aluminium silicates). Diatomaceous earth is made up primarily of amorphous or shapeless silica (silicon dioxide) secreted by diatoms. Preferably, the diatomaceous earth has an average particle size of from about 1 micron to about 50 microns, more preferably from about 5 microns to about 25 microns, and most preferably from about 5 microns to about 15 microns. Particles smaller than 1 micron in diameter are not considered in determining the "average particle size" of diatomaceous earth particles in a diatomaceous earth sample.

Without limiting the operating mechanism of the coating layers of the present invention, it is believed that the sharp edges inherent to diatomaceous earth act to irritate or cut the larvae or adult insects that traverse the coating layer. Thus, in one embodiment, the coating formulations and coating layers include an insect-cutting material and/or a larva-cutting material. This irritating or cutting action is believed to facilitate hormone delivery to a target organism. As a result, the hormone effects on the target organism can be increased while allowing for decreased hormone concentrations in the coating layer. The diatomaceous earth that can be implemented in the present invention may originate from mud, seaweed, stagnant water, fresh water or salt water sources. If diatomaceous earth is included in the coating layer, the coating layer preferably comprises from about 0.01 weight percent to about 20 weight percent, more preferably from about 0.01 weight percent to about 10 weight percent, and most preferably from about 0.1 weight percent to about 5 weight percent of diatomaceous earth. Experimental evidence, provided below, indicates that the combination of a hormone with diatomaceous earth in a coating layer yields synergistic, surprising and unexpected results over what would be expected by one of ordinary skill in the art based on the effects of these individual components on larvae development and reproductive ability.

As indicated above, the coating compositions of the present invention preferably are implemented in human and animal food packaging materials in order to safely and efficiently protect the foodstuffs contained therein from insect infestation. Thus, the coating layer preferably is disposed or adhered on an external surface of a substrate containing human, or animal food. An exemplary list of substrates includes cardboard, cloth, bags, wrappers, wood, paper, plastic, and combinations thereof. Specific examples of substrates include food wrappers, cloth bags, bleached paper, clay coated paper, bleached clay coated paper, metalized paper, corrugated boxes, crates, contact paper, shelf paper, and paper linings. In one preferred embodiment, the substrate is a bag such as a wheat or grain storage bag, a burlap bag, a plastic bag, a cloth bag (e.g., formed of cotton or any other textile), or a dog or cat food bag.

The substrate also may include a seal between two materials of the same or different composition. As a result of small, possibly microscopic, openings oriented about packaging seals, food storage containers are especially vulnerable to insect penetration. Glue and/or thread or string are often used to minimize insect contamination along packaging seals. In one embodiment of the present invention, the coating formulation further includes a glue material, e.g., "hot melt" or a polyamide glue, which is applied to one or more of the materials that form the package seal. Thus, in this embodiment, glue and/or thread mechanically limits insect penetration and the hormone in the glue further acts to minimize or eliminate product contamination by reducing insect viability. Additionally or alternatively, the coating material is applied to the sealing thread or string, which may be grasped and pulled by an end user to open the food package. Preferably, the thread or string is arranged in a sack knot configuration. The thread or string acts to break through glue lines and allow the end user to access the foodstuff contained in the package.

The coating layers of the present invention may also be incorporated in a laminate material having a plurality of layers. Insects often bore through external layers and, typically, oviposition occurs between layers of a multi-layered material. Accordingly, the coating of the present invention preferably is oriented between layers to facilitate delivery of the hormone active ingredient to any eggs or larvae that develop between the layers. In this embodiment, a coating formulation according to the present invention may be applied to a substrate layer. The formulation is then cured (in the UV embodiment) or the polymer carrier is removed (in solvent based formulations) thereby forming a substantially solid coating layer. A second layer then may be secured to the substrate layer with an adhesive composition, by heat fusing, or by other known lamination techniques. In this embodiment, the hormone-containing coating layer is oriented between the substrate and the second layer. Additionally or alternatively, the coating layer may be formed on the interior surface of the substrate layer and/or on the external surface of the second layer. In other embodiments, the multi-layer material includes more than two layers in addition to one or more coating layers according to the present invention.

The present invention is also directed to various methods for preparing coating formulations and for applying the coating formulations to substrates to form coating layers. In one embodiment, the method includes the steps of: (a) providing a substrate having an external surface; (b) providing a liquid coating material, e.g., coating formulation, comprising from about 5 weight percent to about 30 weight percent of a monomer, from about 0.1 to about 15 weight percent of a tertiary amine, from about 1 wppm to about 100,000 wppm of a hormone, and from about 0.1 weight percent to about 20 weight percent of a photoinitiator; (c) applying the liquid coating material to the external surface of the substrate to form an uncured coated substrate; and (d) subjecting the uncured coated substrate to radiation under conditions effective to form a cured coated substrate. The hormone in the liquid coating material may be a juvenile hormone, an ecdysone agonist, an ecdysteroid, or a chitin synthesis inhibitor. Preferably, the hormone is a juvenile hormone selected from the group consisting of: hydroprene, methoprene, dimilin and fenoxycarb. Preferably, the hormone included in the coating formulation is a liquid.

The step of applying the liquid coating material to the external surface of the substrate to form an uncured coated substrate may include rolling the liquid coating material onto the external surface of the substrate with a rolling device. Optionally, the coating formulations are applied onto a substrate by rod coater, blade coater, air knife coater, roll coater, multiple roll transfer, controlled and uncontrolled drip, wet bath dip, curtain coater, and vacuum and non-vacuum impregnation. Particularly if one or more inks are included in the coating formulation, the coating formulation preferably is applied onto a substrate by gravure, rotogravure, flexographic, screen, letterpress, web offset, sheetfed, offset or ink jet printing processes. Additionally or alternatively, the applying step comprises spraying the liquid coating material onto the external surface of the substrate with a spraying device having a spraying nozzle.

In the step of subjecting the uncured coated substrate to radiation under conditions effective to form a cured coated substrate, the radiation preferably is selected from the group consisting of ultraviolet, X-Ray, visible light, and thermal radiation. Preferably, the liquid coating material is cured by UV radiation.

In one embodiment, referred to herein as the solvent-based formulation embodiment, the invention is directed to a method for forming a coating layer on a substrate, wherein the polymer in the coating layer is formed prior to applying the liquid coating material, e.g., coating formulation, onto a substrate. In one embodiment, the method includes providing a substrate having an external surface; providing a liquid coating material comprising a polymer, a polymer carrier (e.g., a solvent), and from about 1 wppm to about 100,000 wppm of a hormone; applying the liquid coating material to the external surface of the substrate to form a liquid coated substrate; and removing the polymer carrier from the liquid coated substrate under conditions effective to form a solid coated substrate. The applying step may be performed by any of the applying techniques described above. The hormone in the liquid coating material may be a juvenile hormone, an ecdysone agonist, an ecdysteroid, or a chitin synthesis inhibitor. Preferably, the hormone is a juvenile hormone selected from the group consisting of: hydroprene, methoprene, dimilin and fenoxycarb. The step of removing the polymer carrier preferably comprises heating the liquid coated substrate under conditions effective to at least partially vaporize the polymer carrier. The heat required to remove the polymer carrier will vary greatly depending on the volatility of the polymer carrier chosen. Preferably, the liquid coated substrate is heated from about 75° F. (24° C.) to about 300° F. (149° C.), more preferably from about 75° F. (24° C.) to about 200° F. (93° C.), and most preferably from about 75° F. (24° C.) to about 150° F. (66° C.). Ideally, the heating is provided from about 5 to about 45 seconds, more preferably from about 5 to about 30 seconds, and most preferably from about 5 to about 15 seconds.

A non-limiting list of exemplary polymer carriers includes: water (deionized and/or tap), alkanes, alcohols, ketones, glycol ethers, oxygenated solvents, organic solvents, halogenated solvents such as chlorinated solvents, acetone, butanol, butyl acetates, heptane, isopropanol, methyl ethyl ketone, toluene and xylenes. In this embodiment, the coating formulation also preferably includes from about 1 weight percent to about 99 weight percent, more preferably from about 20 weight percent to about 80 weight percent, and most preferably from about 30 weight percent to about 70 weight percent of a polymer. The coating formulation also preferably includes from about 5 weight percent to about 90 weight percent, more preferably from about 30 weight percent to about 75 weight percent, and most preferably from about 40 weight percent to about 60 weight percent of a polymer carrier.

The invention is also directed to a coating formulation (and to processes for forming such coating formulations) that is formed, at least in part, from a polymer-containing emulsion comprising a polymer and a polymer carrier (e.g., an emulsifying agent). Preferably, the polymer in the polymer-containing emulsion is formed before the coating formulation is prepared. In this embodiment, the polymer-containing emulsion comprises a polymer such as polystyrene, acrylated polymers, polyurethane, or any other of the polymers listed above. Optionally, the polymer-containing emulsion is an acrylic emulsion, a polyurethane emulsion, a styrenated acrylic emulsion, an acrylic resin solution, or a styrene acrylic resin solution. The polymer carrier in this embodiment preferably is not readily miscible with the polymer in order to form the emulsion. The polymer carrier may comprise ammonium hydroxide or any other of the polymer carriers listed above.

One preferred polymer-containing emulsion suitable for use according to the present invention is marked under the trade name Joncryl 2178 and comprises styrene acrylic polymers, about 28 weight percent ammonium hydroxide, and polypropylene glycol. Joncryl 2178 also provides excellent anti-blocking properties, gloss and rub resistance. Preferably, the coating formulation comprises from about 25 weight percent to about 99 weight percent, preferably from about 51 weight percent to about 99 weight percent, more preferably from about 72 to about 74 weight percent, and ideally about 73 weight percent Joncryl 2178.

The coating formulation of this embodiment also preferably comprises some amount of water (preferably deionized) to provide the coating formulation with desirable fluidization characteristics. The water also acts as a rheology modifier. The coating formulation optionally comprises from about 0.1 to about 50 weight percent, from about 0.1 to about 15 weight percent, preferably from about 4.09 to about 4.18 weight percent deionized water, and most preferably about 4.14 weight percent deionized water. It has been discovered that a coating formulation comprising about 73 weight percent Joncryl 2178 and about 4 weight percent water provides desirable fluidization characteristics suitable for applying the coating formulation onto a substrate In one embodiment, the coating formulation also includes an aqueous crosslinking agent such as a zinc oxide solution, which provides improved film hardness and heat resistance, a carboxyl group crosslinking agent, or a metal crosslinking agent. Preferably the coating formulation comprises from about 0.1 to about 20 weight percent or from about 0.1 to about 10 weight percent crosslinking agent. Preferably, the coating formulation comprises from about 4.95 to about 5.05 weight percent crosslinking agent, and most preferably about 5.0 weight percent crosslinking agent. The preferred zinc oxide solution preferably comprises from about 60 to about 65 weight percent water (CAS No. 7732-18-5) and from about 35 to about 40 weight percent zinc ammonium carbonate (CAS No. 40861-29-8).

In this embodiment, the coating formulation also optionally comprises a nonionic defoamer, surfactant, or antifoaming agent, discussed above. One preferred non-ionic defoamer is distributed under the trade name Surfynol DF-70, which comprises 6 weight percent 1, 1-24, 1-31, and 2 distilled tall fatty acids (CAS No. 084133506). DF-70 is a 100 percent active organic defoamer that is designed to provide knockdown defoaming and sustained antifoaming in water-based formulations. If included in the coating formulation, then the coating formulation preferably comprises from about 0.001 to about 5 weight percent, from about 0.01 to about 3 weight percent, preferably from about 0.198 to about 0.202 weight percent of nonionic defoamer, and most preferably about 0.20 weight percent nonionic defoamer.

One or more slip modifying components also may be included in the coating formulation in order to provide desirable slip resistance characteristics (e.g., coefficient of friction and slide angle) for the resulting coating layer. In one embodiment, the slip modifying component comprises a water dispersible silicone additive such as Q2-3238, silicone, water soluble silicone, or dimethyl siloxane hydroxy-terminated silicone. Q2-3238 comprises a 17 weight percent solution of ethoxylated C12-C14 secondary alcohols (CAS No. 084133506) and provides desirable coefficient of friction and slide angle characteristics in addition to contributing to overall anti-blocking properties and rub resistance. Preferably, the coating formulation comprises from about 0.001 to about 5 weight percent, from about 0.01 to about 5 weight percent, preferably from about 0.247 to about 0.252 weight percent, and most preferably about 0.25 weight percent Q2-3238. Additionally or alternatively, the coating formulation optionally comprises from about 0.01 to about 10 weight percent, from about 0.1 to about 5 weight percent, preferably from about 0.82 to about 0.84 weight percent, and most preferably about 0.83 weight percent of fumed silica, hydrophobic fumed silica, synthetic amorphous silicon dioxide, or a treated silica additive such as Aerosil R-812. Aerosil R-812 comprises hexamethyl-disilazane treated silica (CAS No. 68909-20-6) and provides desirable coefficient of friction and slide angle characteristics. Aerosil R-812 also contributes to overall anti-blocking properties.

In one embodiment, the coating formulation comprises a polyethylene wax emulsion or dispersion, a polypropylene wax emulsion or dispersion, a PTFE wax dispersion, or a microcrystaline wax dispersion for providing desirable rub resistance characteristics. One preferred polyethylene wax emulsion is manufactured under the trade name Jon Wax 26 and comprises from about 70 to about 75 weight percent water (CAS No. 7732-18-5), from about 20 to about 25 weight percent paraffin wax (CAS No. 68441-17-8), from about 1 to about 3 weight percent diethylaminoethanol (CAS No. 100-37-8), and from about 1 to about 3 weight percent oleic acids (CAS No. 112-80-1). Preferably, the coating formulation comprises from about 1 to about 40 weight percent, from about 1 to about 25 weight percent, from about 16.50 to about 16.62 weight percent, and most preferably about 16.56 weight percent of a polyethylene or polypropylene wax emulsion such as Jon Wax 26.

Thus, in one embodiment, the invention is directed to a coating formulation, which includes from about 25 to about 99 weight percent of a polymer containing emulsion, from about 0.1 to about 20 weight percent of an aqueous crosslinking agent, from about 0.001 to about 5 weight percent of a defoamer, from about 1 to about 40 weight percent of a polyethylene wax emulsion or of a polypropylene wax emulsion, and from about 1 wppm to about 100,000 wppm of a hormone (preferably about 10 wppm or 100 wppm of a hormone). Optionally, the coating formulation further contains from about 0.1 to about 50 weight percent deionized water. The polymer containing emulsion optionally comprises styrene acrylic polymers, ammonium hydroxide and polypropylene glycol.

In another embodiment, the invention is to a method, which comprises providing a substrate having an external surface; providing a liquid coating material comprising a polymer, a polymer carrier (e.g., an emulsifying agent or solvent), optionally a crosslinking agent, and from about 1 wppm to about 100,000 wppm of a hormone; applying the liquid coating material to the external surface of the substrate to form a liquid coated substrate; and removing the polymer carrier from the liquid coated substrate under conditions effective to form a solid coated substrate. The applying step may be performed by any of the applying techniques described above. The hormone in the liquid coating material may be a juvenile hormone, an ecdysone agonist, an ecdysteroid, or a chitin synthesis inhibitor. Preferably, the hormone is a juvenile hormone selected from the group consisting of: hydroprene, methoprene, dimilin and fenoxycarb. The step of removing the polymer carrier preferably comprises heating the liquid coated substrate under conditions effective to at least partially vaporize the polymer carrier. The heat required to remove the polymer carrier will vary greatly depending on the volatility of the polymer carrier chosen. Preferably, the liquid coated substrate is heated from about 75° F. (24° C.) to about 300° F. (149° C.), more preferably from about 75° F. (24° C.) to about 200° F. (93° C.), and most preferably from about 75° F. (24° C.) to about 150° F. (66° C.). Ideally, the heating is provided from about 5 to about 45 seconds, more preferably from about 5 to about 30 seconds, and most preferably from about 5 to about 15 seconds.

In another embodiment, the invention is to a method for forming a hormone coating composition from a polymer emulsion. In this embodiment, a substrate is provided having an external surface. A liquid coating material is also provided comprising a polymer emulsion, and from about 1 wppm to about 100,000 wppm of a hormone. The polymer emulsion comprises a polymer and an emulsifying agent. The liquid coating material is applied to the external surface of the substrate to form a liquid coated substrate. The emulsifying agent is removed from the liquid coated substrate under conditions effective to form a solid coated substrate. In this embodiment, the liquid coating material optionally is comprised of from about 25 to about 99 weight percent of the polymer emulsion, from about 0.1 to about 20 weight percent of an aqueous crosslinking agent, from about 0.001 to about 5 weight percent of a defoamer, and from about 1 to about 40 weight percent of a polyethylene wax emulsion or of a polypropylene wax emulsion.

In another embodiment, the method of the present invention includes combining, in any order, a monomer emulsion, a photoinitiator and a juvenile hormone to form a juvenile hormone emulsion. The juvenile hormone emulsion includes from about 10 weight percent to about 80 weight percent of the monomer emulsion, from about 0.1 weight percent to about 20 weight percent of the photoinitiator, and from about 1 wppm to about 100,000 wppm of the juvenile hormone. The juvenile hormone emulsion is mixed and applied onto a substrate. The mixing optionally comprises mixing in a mechanical mixer, e.g., at a rate of from about 50 to 10,000 rpm, more preferably from about 500 to about 5000 rpm, and most preferably from about 1000 to 2000 rpm. Preferably, the temperature of the emulsion during mixing is from about 60° F. (16° C.) to about 140° F. (60° C.), more preferably from about 90° F. (32° C.) to about 120° F. (49° C.), and more preferably from about 100° F. (38° C.) to about 115° F. (46° C.). The juvenile hormone emulsion on the substrate is then exposed to ultraviolet radiation under conditions effective to cure the juvenile hormone emulsion thereby forming the juvenile hormone coating layer.

In another embodiment, the method of the present invention includes providing a substrate having an external surface, and providing a liquid coating material. The liquid coating material includes from about 10 weight percent to about 50 weight percent of an oligomer, from about 0.1 weight percent to about 15 weight percent of a tertiary amine, from about 1 wppm to about 100,000 wppm of a hormone, and from about 0.1 weight percent to about 20 weight percent of a photoinitiator. The liquid coating material is applied to the external surface of the substrate to form an uncured coated substrate, which is subjected to radiation under conditions effective to form a cured coated substrate.

In any of the above-described embodiments, the liquid coating material optionally comprises from about 0.01 weight percent to about 20 weight percent of diatomaceous earth. If diatomaceous earth is included in the liquid coating material, the method preferably includes agitating the liquid coating material under conditions effective to distribute the diatomaceous earth throughout the liquid coating material. Optionally, the liquid coating material further comprises from about 0.1 weight percent to about 15 weight percent of a UV protectant material, e.g., benzophenone. Additionally or alternatively, the liquid coating material further comprises from about 0.1 weight percent to about 20 weight percent of a rheology additive. Cellulose acetate butyrate and cellulose acetate proprionate are particularly preferred rheology additives.

Additionally, the formulations and/or coatings of the present invention optionally include one or more additional additives. A non-limiting list of exemplary additives includes perfumes, optical whiteners, thickeners, corrosion inhibitors, surfactants, preservatives, tracers, silicones, waxes, inks, pigments, insect attractants such as insect pheromones, biocides, fungicides, fillers, and insect repellants such as those identified in U.S. Pat. No. 5,688,509, the entirety of which is incorporated herein by reference. In one embodiment, the additive includes one or more inorganic materials such as silicate-containing materials. The inclusion of silicates in the coating formulation, particularly in colloidal form, and in the resulting coating layers provides desirable processing, handling and/or adhesive characteristics. If an additive is included in a coating formulation according to the present invention, the coating formulation preferably includes from about 1 to about 75 weight percent, more preferably from about 5 to about 60 weight percent, and most preferably from about 10 to about 40 weight percent of an additive.

The present invention will be better understood in view of the following non-limiting examples.

EXAMPLE 1

Effect of Methoprene at Low Concentrations

Procedure

An experiment was set up to determine the effectiveness of methoprene at very low concentrations on day 16 larvae of the Indian Meal Moth, *Plodia Interpunctella*. The concentrations tested ranged from the control at 0 wppm to 1000 wppm increasing by increments of 10×. Ten larvae per sample were added to the treated paper and exposed throughout the experiment in an incubator (Precision Model No. 815) at 80° F. (27° C.) and at a relative humidity of 60 percent. Behavior, webbing characteristics and survival rates were observed over 19 days.

The coating formulation components (excluding methoprene) and preparation procedure are described in Table 1, below.

TABLE 1

COATING PREPARATION PROCEDURE AND PERCENTCOMPOSITION

| Batch Step | Actual Weight Percentage | Theoretical Weight |
|---|---|---|
| 1. Weigh out photomer 4006 (Cognis) trimethylolpropane triacrylate monomer | 47.17 | 47.2 lbs. (21.4 kg) |
| 2. Add CAB 551-0.01 premix (Actinic) Rheology Additive | 25.00 | 25.0 lbs. (11.3 kg) |
| 3. Add CN120C60 Oligomer (Sartomer) | 13.4 | 13.4 lbs. (6.1 kg) |
| 4 Add Surfynol DF-574 (Air Products) Defoamer | 0.1 | 0.1 lbs. (45.4 g) |
| 5. Add Optiblanc (3 V) Optical Whitener | 0.08 | 0.08 lbs. (36.3 g) |
| 6. Add MDEA (ChemCentral) Coinitiator | 6.38 | 6.4 lbs. (2.9 kg) |
| 7. Add benzophenone (Sartomer) Photoinitiator | 6.87 | 6.9 lbs. (3.1 kg) |
| 8. Methoprene | Varies | Varies |

As the Benzophenone was added to the mixture in step 7, above, the mixture was stirred in a mixer at 1500 rpm and at a temperature of 70° F. (21° C.) until the benzophenone was dissolved. As the methoprene was added to the mixture in step 8, above, the mixture was stirred in a mixer at 1500 rpm and at a temperature of 89° F. (32° C.).

Behavior

As the level of treatment increased, the larvae became increasingly aggressive. The larvae in the control appeared content with one another throughout the 19 days of the testing period. However, the exposed larvae showed signs of aggression, e.g., increased nipping and cannibalism, as early as day 4 of the testing period.

Webbing Characteristics

Webbing is a normal process of the Indian Meal Moth in the pre-pupal stage. The webbing patterns for the control compared to the different levels of treatment showed significant changes. The control larvae produced webbing that was thin and evenly dispersed along the edge of the dish. The larvae exposed to 1 wppm methoprene produced webbing that appeared slightly thicker throughout the dish than the control. The larvae exposed to 10 wppm methoprene produced thicker, more centralized webbing. The webbing of the larvae exposed to 10 wppm methoprene, appeared dense and more centralized than the 10 wppm methoprene sample. Ultimately, the larvae exposed to 1000 wppm methoprene produced a completely centralized mound of webbing. FIGS. 1A-1E are images of the webbing patterns at 0 wppm methoprene (control), 1 wppm methoprene, 10 wppm methoprene, 100 wppm methoprene and 1000 wppm methoprene, respectively.

Survival Rate

Figure 1A:
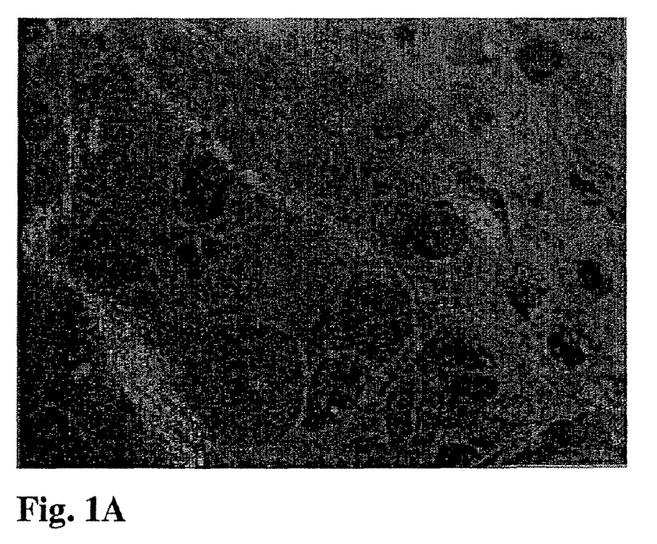
FIGS. 1A-1E are photographs showing the webbing characteristics of Indian Meal Moth larvae after having been exposed to coating layers with varying methoprene concentrations.
Figure 1B:
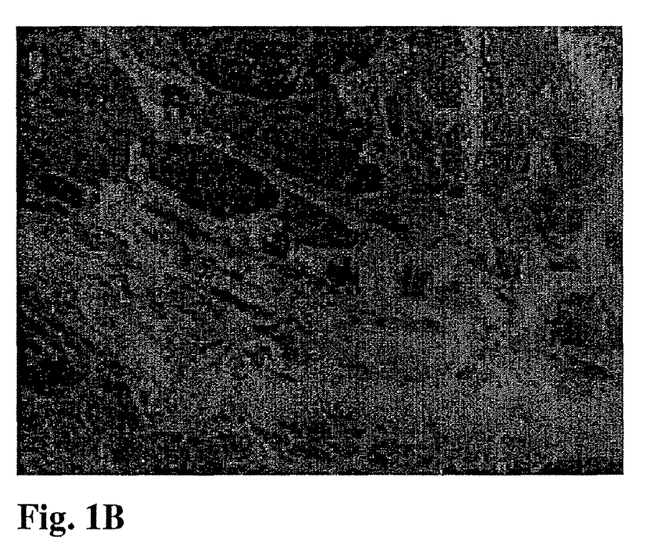
Figure 1C:
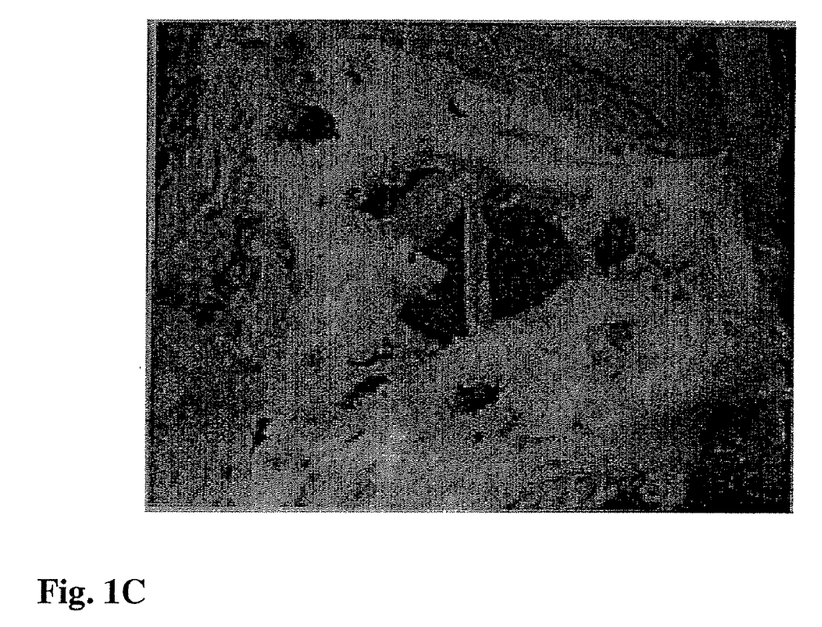
Figure 1D:
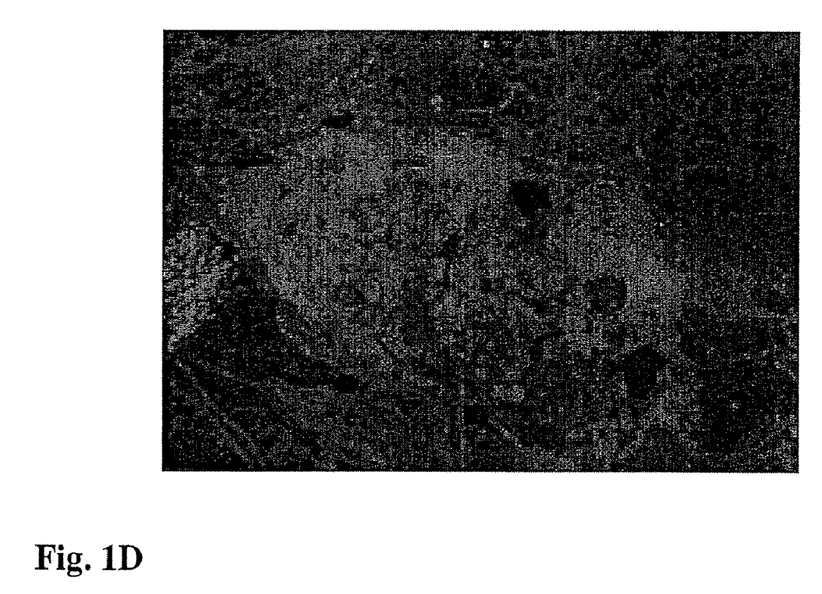
Figure 1E:
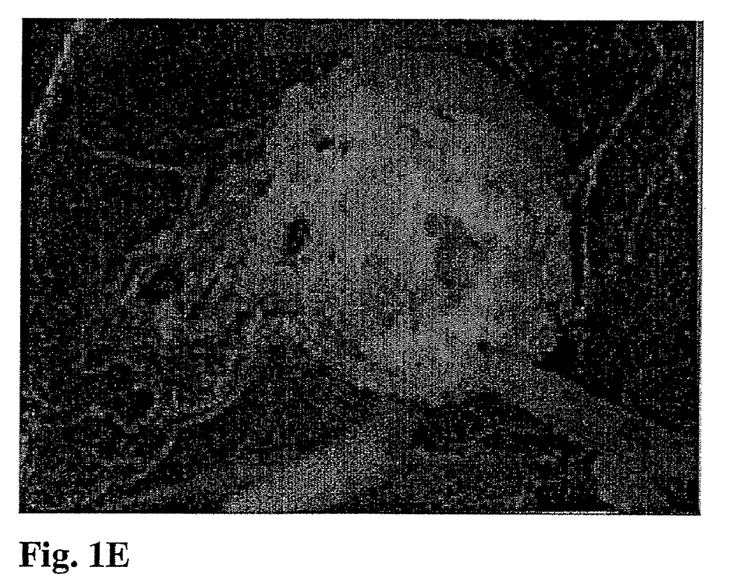
Figure 2:
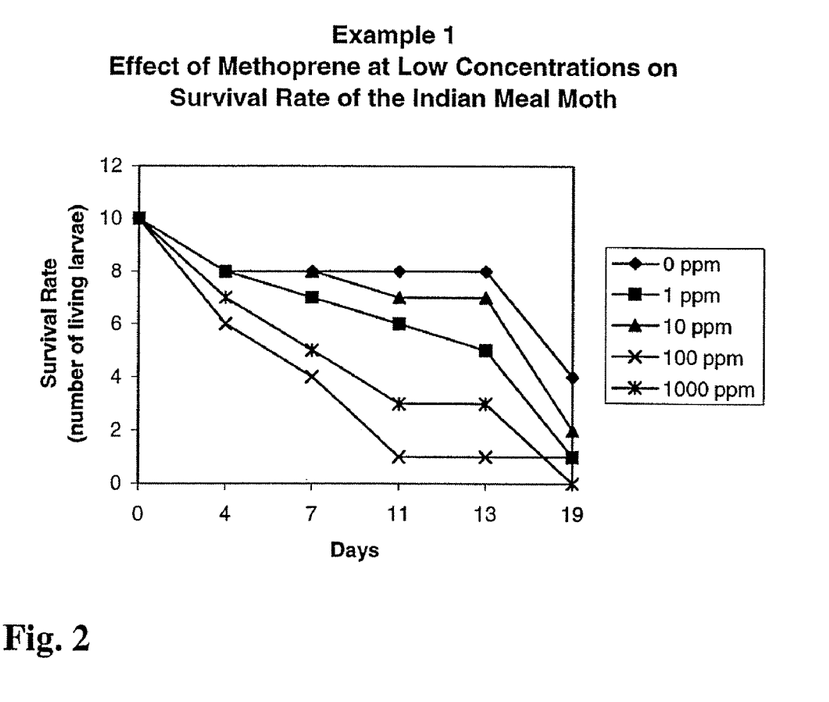
FIG. 2 is a graph that plots the survival rate of Indian Meal Moth larvae against exposure time in days.

Complete metamorphosis of the Indian Meal Moth takes three to six weeks depending on diet, temperature and relative humidity. The larvae were confined to a small area with no food, therefore a higher death rate was expected sooner. Treatment levels as low as 1 wppm showed a significant decrease in survival rate compared to the control sample. Table 2, below, provides the survival rates after prolonged exposure to different concentrations of methoprene. FIG. 2 graphically illustrates the results shown in Table 2.

TABLE 2

EFFECT OF METHOPRENE AT LOW CONCENTRATIONS ON THE SURVIVAL RATE* OF THE INDIAN MEAL MOTH

| DAY | CONTROL | 1 wppm | 10 wppm | 100 wppm | 1000 wppm |
|---|---|---|---|---|---|
| 4 | 8 | 8 | 8 | 6 | 7 |
| 7 | 8 | 7 | 8 | 4 | 5 |
| 11 | 8 | 6 | 7 | 1 | 3 |
| 13 | 8 | 5 | 7 | 1 | 3 |
| 19 | 4 | 1 | 2 | 1 | 0 |

*Survival rate is expressed in number of larvae surviving out of 10 larvae per test sample.

EXAMPLE 2

Combining Diatomaceous Earth with Methoprene

Procedure

An experiment was set up to determine the effect of combining diatomaceous earth (DE) with methoprene (MP) in a UV coating layer. Eggs were allowed to hatch and the newly emerged larvae were forced to crawl across a treated sample to reach the food source. The treatment samples included a control (Mw-720), 1 weight percent diatomaceous earth, and 1 weight percent diatomaceous earth combined with methoprene concentrations ranging from 1 wppm to 1000 wppm in increments of 10×. The compositions of the coating layers in this experiment were the same as in Example 1, but also containing diatomaceous earth, as indicated in Table 3, below. Five eggs per dish and three dishes per sample were tested. This experiment focused on the maturation and the offspring produced. Results were obtained over a 31 or 32 day period. A total of fifteen eggs were exposed to each treatment level. From when adults hatched, the number of adults were counted and averaged over the remainder of the experiment. The number of new eggs were also counted and the average number of eggs per adult was calculated. Generally, the average number of adults per day as well as egg production decreased as treatment levels increased.

In the experiment, for each methoprene concentration, the percent decrease in average number of eggs per adult was calculated with respect to the average control sample (treatment number 3). The percent decrease in average number of eggs per adult was also calculated for treatment number 4, which included 1 weight percent diatomaceous earth but no methoprene. For each methoprene concentration, a hypothetical or "expected" percent decrease in average number of eggs per adult was calculated (conservatively) by adding together the percent decrease of treatment number 4 (diatomaceous earth) with each respective methoprene treatment that did not include diatomaceous earth (treatments 5, 8, 11 and 14). Combined test runs (Actual test runs 7, 10, 13 and 16), which included 1 weight percent diatomaceous earth and varying concentrations of methoprene, were then performed. The resulting percent decreases in average number of eggs per adult in the combined test runs were compared to the expected percent decrease. Table 3, below represents data collected over the test period.

TABLE 3

COMBINED EFFECT OF METHOPRENE AND DIATOMACEOUS EARTH IN COATING LAYERS

| Treatment Number | Amount DE (wt. %) | Amount MP (wppm) | Average No of Adults/ Day | Average No of Eggs/ Adults | % Decrease From Avg. Control |
|---|---|---|---|---|---|
| 1 (Ctrl 1) | 0 | 0 | 7 | 17 | N/A |
| 2 (Ctrl 2) | 0 | 0 | 9 | 24 | N/A |
| 3 Avg. Ctrl. | 0 | 0 | 8 | 20.5 | N/A |
| 4 DE | 1 | 0 | 10 | 18 | 12 |
| 5 | 0 | 1 | 10 | 26 | −27 |
| 6 Expected | 1 | 1 | N/A | N/A | −15 |
| 7 Actual | 1 | 1 | 4 | 8 | 61 |
| 8 | 0 | 10 | 10 | 16 | 22 |
| 9 Expected | 1 | 10 | N/A | N/A | 34 |
| 10 Actual | 1 | 10 | 6 | 10 | 52 |
| 11 | 0 | 100 | 8 | 15 | 27 |
| 12 Expected | 1 | 100 | N/A | N/A | 39 |
| 13 Actual | 1 | 100 | 9 | 13 | 37 |
| 14 | 0 | 1000 | 10 | 13 | 37 |
| 15 Expected | 1 | 1000 | N/A | N/A | 49 |
| 16 Actual | 1 | 1000 | 5 | 0 | 100 |

Results

As can be seen from the results provided in Table 3, for actual treatment number 7 (1 wppm+1 wt. percent methoprene), a 61 percent decrease in average number of eggs per adult from average control was realized. This result was also far superior to the expected percent decrease from average control of −15 percent. For actual treatment number 10 (10 wppm+1 wt. percent methoprene), a 52 percent decrease from average control was realized. This result was superior to the expected decrease of 34 percent. For actual treatment number 13 (100 wppm+1 wt. percent methoprene), a 37 percent decrease from average control was realized. This result was within experimental error of the expected decrease of 39 percent. For actual treatment number 16 (1000 wppm+1 wt. percent methoprene), a 100 percent decrease from average control was realized. This result was far superior to the expected decrease of 49 percent. The results above surprisingly and unexpectedly indicate that a synergistic result was realized by combining methoprene, at low concentrations, with diatomaceous earth in coating layers. Overall, the samples containing diatomaceous earth alone and those containing methoprene alone proved far less effective than samples containing both diatomaceous earth and methoprene.

EXAMPLE 3

Exposure of 16 Day Larvae to Methoprene

Figure 3:
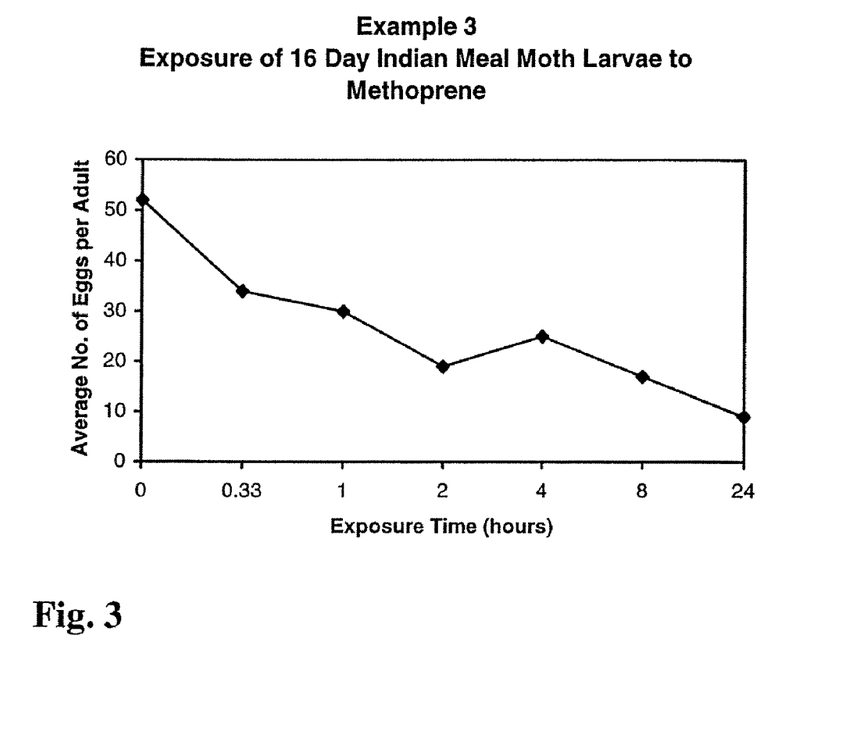
FIG. 3 is a graph that plots average number of eggs per Indian Meal Moth adult against exposure time.

An experiment was set up to determine the effect of exposing 16 day Indian Meal Moth larvae to methoprene for varying periods of time. The treatment levels tested were control at 0 wppm methoprene and 1000 wppm methoprene. Five larvae (3 females, 2 males) per sample were added to paper treated with the coating composition described in Example 1. The larvae were exposed to the samples for different amount of time. The times of exposure were 0 hrs., 20 min., 1 hr., 2 hrs., 4 hrs., 8 hrs., and 24 hrs. After larvae were exposed for the set amount of time, they were placed in an incubator (Precision Model No. 815) at 80° F. (27° C.) and at a relative humidity of 60 percent, where they were allowed to pupate, become adults, and reproduce. Observations were obtained throughout a 16 day period. Table 4, below, represents data collected over the test period. From when adults hatched, the number of adults were counted and averaged over the remainder of the experiment. The number of new eggs were also counted and the average number of eggs per adult was calculated. Generally, egg production decreased as treatment levels increased. FIG. 3 graphically illustrates the results shown in Table 4.

TABLE 4

VARYING METHOPRENE EXPOSURE PERIODS

| Time Exposed | Treatment (wppm MP) | Average No. of Adults/Day | Average No. of Eggs/Adult |
|---|---|---|---|
| 0 | 0 | 9 | 52 |
| 20 min | 1000 | 10 | 34 |
| 1 hr. | 1000 | 12 | 30 |
| 2 hrs. | 1000 | 12 | 19 |
| 4 hrs. | 1000 | 10 | 25 |
| 8 hrs. | 1000 | 9 | 17 |
| 24 hrs. | 1000 | 7 | 9 |

EXAMPLE 4

Adult Exposure to Liquid Methoprene

An experiment was set up to determine how egg production would be affected when Indian Meal Moth adults were exposed to liquid methoprene in a UV coating. Adults were allowed to emerge into jars lined with treated paper. The treatment levels tested were a control at 0 wppm to 1000 wppm increasing by increments of 10×. A combination treatment of liquid methoprene at 1000 wppm and 1 weight percent diatomaceous earth was also tested. The eggs produced fell to a treated surface before being collected and placed into rearing food. Observations and egg collections were taken over a 15 day period.

Table 5, below, shows the total number of adults that emerged over the 15-day observation period. The adults came from stock insects and the number exposed per treatment was not predetermined. The total number of eggs represents all eggs per treatment collected over 8 days. The total number of viable eggs represents the number of eggs that hatched. These larvae were allowed to feed for 14 days before counting.

TABLE 5

ADULT EXPOSURE TO METHOPRENE

| Treatment | Total No. of Adults | Total No. of Eggs | Total No. of Viable Eggs | Percent Viable Eggs | Total Percent Reduction |
|---|---|---|---|---|---|
| 0 wppm MP | 211 | 2270 | 1188 | 52 | N/A |
| 10 wppm MP | 226 | 1430 | 108 | 7.5 | 85.6 |
| 100 wppm MP | 201 | 1285 | 234 | 18 | 65.4 |
| 1000 wppm MP | 135 | 1190 | 432 | 36 | 30.8 |
| 1 wt. % DE & 1000 wppm MP | 208 | 1420 | 234 | 16 | 69.2 |

This experiment shows that treating Indian Meal Moths as adults results in a significant decrease in the total population. The average reduction for each treatment compared to the control was 60 percent.

Having now fully described the invention, it will be appreciated by those skilled in the art that the invention can be performed within a wide range of parameters within what is claimed without departing from the spirit and scope of the invention.

We claim:

1. A controlled release hormone composition, comprising:
a substrate having an external surface; and
a coating layer disposed on the external surface, the coating layer comprising a polymer web, from about 1 wppm to about 100,000 wppm of a hormone comprising pyriproxyfen dispersed throughout the polymer web, and from about 0.1 weight percent to about 20 weight percent of a cellulose acetate composition.

2. The hormone composition of claim 1, wherein the cellulose acetate composition is dispersed throughout the polymer web.

3. The hormone composition of claim 1, wherein the cellulose acetate composition is selected from the group consisting of: cellulose acetate butyrate and cellulose acetate proprionate.

4. The hormone composition of claim 1, further comprising:
from about 0.1 weight percent to about 20 weight percent diatomaceous earth.

5. The hormone composition of claim 1, wherein the coating layer includes from about 0.1 weight percent to about 15 weight percent of a UV protectant material.

6. The hormone composition of claim 1, further comprising from about 0.1 weight percent to about 15 weight percent of a co-initiator.

7. The hormone composition of claim 6, wherein the co-initiator is a tertiary amine.

8. The hormone composition of claim 1, further comprising a second layer comprising substantially no hormone, wherein the second layer is oriented externally to the coating layer or between the coating layer and the substrate.

9. A hormone composition, comprising:
a substrate having an external surface; and
a coating layer disposed on the external surface comprising from about 1 wppm to about 100,000 wppm of a hormone comprising pyriproxyfen dispersed throughout a polymer web, a photoinitiator, and from about 0.01 weight percent to about 20 weight percent diatomaceous earth also dispersed throughout the polymer web.

10. The hormone composition of claim 9, wherein the coating layer includes from about 0.1 weight percent to about 15 weight percent of a UV protectant material.

11. The hormone composition of claim 9, further comprising from about 0.1 weight percent to about 15 weight percent of a co-initiator.

12. The hormone composition of claim 11, wherein the co-initiator is a tertiary amine.

13. The hormone composition of claim 9, further comprising a second layer comprising substantially no hormone, wherein the second layer is oriented externally to the coating layer or between the coating layer and the substrate.

14. A method for forming a hormone composition, the method comprising the steps of:
(a) providing a substrate having an external surface;
(b) providing a liquid coating material comprising from about 10 weight percent to about 80 weight percent of a monomer, from about 0.1 weight percent to about 15 weight percent of a tertiary amine, from about 1 wppm to about 100,000 wppm of a hormone comprising pyriproxyfen, and from about 0.1 weight percent to about 20 weight percent of a photoinitiator;
(c) applying the liquid coating material to the external surface of the substrate to form an uncured coated substrate; and
(d) subjecting the uncured coated substrate to radiation under conditions effective to form a cured coated substrate.

15. The method of claim 14, wherein the liquid coating material further comprises from about 0.01 weight percent to about 20 weight percent of diatomaceous earth.

16. The method of claim 15, further comprising the step of:
(e) agitating the liquid coating material under conditions effective to distribute the diatomaceous earth throughout the liquid coating material.

17. The method of claim 14, wherein the liquid coating material further comprises from about 0.1 weight percent to about 15 weight percent of a UV protectant material.

18. The method of claim 17, wherein the UV protectant material is benzophenone.

19. The method of claim 14, wherein the liquid coating material further comprises from about 0.1 weight percent to about 20 weight percent of a rheology additive.

20. The method of claim 19, wherein the rheology additive is selected from the group consisting of: cellulose acetate butyrate and cellulose acetate proprionate.

21. The method of claim 14, wherein the applying step comprises rolling the liquid coating material onto the external surface of the substrate with a rolling device.

22. The method of claim 14, wherein the applying step comprises spraying the liquid coating material onto the external surface of the substrate with a spraying device.

23. The method of claim 14, wherein the radiation is selected from the group consisting of: UV, X-Ray, visible light, and thermal radiation.

24. The method of claim 14, wherein the radiation is UV radiation.

25. A method for forming a hormone coating composition, the method comprising the steps of:
(a) providing a substrate having an external surface:
(b) providing a liquid coating material comprising a polymer, a polymer carrier, a UV protectant, and from about 1 wppm to about 100,000 wppm of a hormone comprising pyriproxyfen;
(c) applying the liquid coating material to the external surface of the substrate to form a liquid coated substrate; and
(d) removing the polymer carrier from the liquid coated substrate under conditions effective to form a solid coated substrate.

26. The method of claim 25, wherein the liquid coating material further comprises from about 0.01 weight percent to about 20 weight percent diatomaceous earth.

27. The method of claim 26, further comprising the step of:
(e) agitating the liquid coating material under conditions effective to distribute the diatomaceous earth throughout the liquid coating material.

28. The method of claim 25, wherein the liquid coating material further comprises from about 0.1 weight percent to about 20 weight percent of a rheology additive.

29. The method of claim 28, wherein the rheology additive is selected from the group consisting of: cellulose acetate butyrate and cellulose acetate proprionate.

30. The method of claim 25, wherein the liquid coating material further comprises from about 0.1 weight percent to about 15 weight percent of the UV protectant.

31. The method of claim 30, wherein the UV protectant is benzophenone.

32. The method of claim 25, wherein the applying step comprises rolling the liquid coating material onto the external surface of the substrate with a rolling device.

33. The method of claim 25, wherein the applying step comprises spraying the liquid coating material onto the external surface of the substrate with a spraying device.

34. The method of claim 25, wherein the removing step comprises heating the liquid coated substrate under conditions effective to at least partially vaporize the polymer carrier.

35. The method of claim 25, wherein the liquid coating composition is an ink, and wherein the applying comprises printing.

36. A method for formulating a juvenile hormone coating layer, the method comprising the steps of:
(a) combining a monomer emulsion, a photoinitiator and a juvenile hormone comprising pyriproxyfen to form a juvenile hormone emulsion comprising from about 10 weight percent to about 80 weight percent of the monomer emulsion, from about 0.1 weight percent to about 20 weight percent of the photoinitiator, and from about 1 wppm to about 100,000 wppm of the juvenile hormone;
(b) mixing the juvenile hormone emulsion;
(c) applying the juvenile hormone emulsion onto a substrate; and
(d) exposing the juvenile hormone emulsion on the substrate to ultraviolet radiation under conditions effective to cure the juvenile hormone emulsion thereby forming the juvenile hormone coating layer.

37. A method for forming a hormone composition, the method comprising the steps of:
(a) providing a substrate having an external surface;
(b) providing a liquid coating material comprising from about 10 weight percent to about 50 weight percent of an oligomer, from about 0.1 weight percent to about 15 weight percent of a tertiary amine, from about 1 wppm to about 100,000 wppm of a hormone comprising pyriproxyfen, and from about 0.1 weight percent to about 20 weight percent of a photoinitiator;
(c) applying the liquid coating material to the external surface of the substrate to form an uncured coated substrate; and
(d) subjecting the uncured coated substrate to radiation under conditions effective to form a cured coated substrate.

* * * * *